(12) United States Patent
Kwak et al.

(10) Patent No.: US 6,429,319 B1
(45) Date of Patent: Aug. 6, 2002

(54) CONTINUOUS PROCESS FOR THE PRODUCTION OF OPTICALLY PURE (S)-BETA-HYDROXY-GAMMA-BUTYROLACTONE

(75) Inventors: Byong-Sung Kwak; Ki-Nam Chung; Tae-Yun Kim; Ki-Ho Koh; Jin-Woong Kim; Choon-Gil Kim, all of Taejon (KR)

(73) Assignee: SK Corporation, Seoul (KR)

( * ) Notice: Subject to any disclaimer, the term of this patent is extended or adjusted under 35 U.S.C. 154(b) by 84 days.

(21) Appl. No.: 09/767,668

(22) Filed: Jan. 22, 2001

(30) Foreign Application Priority Data

Jul. 27, 2000 (KR) ......................................... 2000-43472

(51) Int. Cl.$^7$ ........................................... C07D 307/56
(52) U.S. Cl. ...................................................... 549/313
(58) Field of Search ........................................ 549/313

(56) References Cited

U.S. PATENT DOCUMENTS

| | | | |
|---|---|---|---|
| 5,292,939 A | 3/1994 | Hollingsworth | 562/515 |
| 5,319,110 A | 6/1994 | Hollingsworth | 549/313 |
| 5,374,773 A | 12/1994 | Hollingsworth | 562/515 |
| 5,473,104 A | 12/1995 | McCarthy | 562/567 |
| 5,808,107 A | 9/1998 | Hollingsworth | 549/323 |
| 5,998,633 A | 12/1999 | Jacks et al. | 549/313 |

*Primary Examiner*—Amelia Owens
(74) *Attorney, Agent, or Firm*—Abelman, Frayne & Schwab

(57) ABSTRACT

Disclosed is a process for the production of optically pure (S)-beta-hydroxy-gamma-butyrolactone through the hydrogenation of substituted carboxylic acid derivatives. A solution containing 1 to 50% by weight of a substituted carboxylic acid derivative is fed at a WHSV of 0.1 to 10 h$^{-1}$, to a fixed bed reactor which is filled with a catalyst and maintained at a reaction temperature of 50 to 550° C. under a halogen partial pressure of 15 to 5,500 psig. The catalyst is composed of a noble metal as a catalytically effective ingredient which is impregnated in an inorganic oxide as a support. The molar ratio of the hydrogen to the substituted carboxylic acid derivative is maintained at a molar ratio of 1:1 to 10:1. The process can produce optically pure (S)-beta-hydroxy-gamma-butyrolactone with higher purities at higher yields than can conventional techniques. In addition to being relatively simple and environmentally friendly, the process is so economically favorable as to apply to industrial production.

13 Claims, 1 Drawing Sheet

CONTINUOUS PROCESS FOR THE PRODUCTION OF OPTICALLY PURE (S)-BETA-HYDROXY-GAMMA-BUTYROLACTONE

BACKGROUND OF THE INVENTION

1. Field of the Invention

The present invention relates to a process for the production of optically pure (S)-beta-hydroxy-gamma-butyrolactone in a continuous manner. More particularly, the present invention relates to a continuous process for the production of optically pure (S)-beta-hydroxy-gamma-butyrolactone by hydrogenation of substituted carboxylic acid derivatives in a fixed-bed reactor which is filled with a catalyst comprising a noble metal and a support.

2. Description of the Prior Art

Optically pure, substituted gamma-butyrolactone is used as an intermediate for the synthesis of a variety of compounds, including medicines such as L-carnitine and ECHB (ethyl (S)-4-cyano-3-hydroxybutyrate), agricultural chemicals, chemical seasonings, and flavorings (U.S. Pat. No. 5,473,104).

Synthesis processes of (S)-β-hydroxy-γ-butyrolactone can be found in many patents. For example, U.S. Pat. Nos. 5,292,939, 5,319,110 and 5,374,773 disclose preparation method of substituted gamma-butyrolactone by the oxidation of water-soluble hydrocarbons. This process, however, is disadvantageous in that the heat of reaction is too great to conduct the oxidation in high concentrations of the reactant. No separation processes, except chromatography, are described in the above patents. Also, nowhere are mentioned yields. Thus, the processes disclosed in the above patents are not suitable for use in the industrial production.

There are reported multi-step processes for preparing gamma-butyrolactone using L-malic acid or L-aspartic acid as a starting material (J. Org. Chem. 1981, 46, 4319; Synth, Commun. 1986, 16, 183). They, however, have a drawback in that optical activity of intermediates is not maintained during the reaction, in addition to being unsuitable for large-scale production.

Starting from (S)-malic acid ester derivatives, a reducing process for preparing gamma-butyrolactone by use of borane-dimethylsulfide and sodium borohydride has been reported (Chem. Lett. 1984, 1389). However, this process is of a batch type with high production costs and being difficult to apply for industrial production. In addition, the reducing process produces wastes in large quantities, which are detrimental to the environment.

A process disclosed in U.S. Pat. No. 5,808,107 is to prepare optically active (S)-beta-hydroxy-gamma-butyrolactone by reducing L-malic acid dimethyl ester with lithium chloride and sodium borohydride to give (S)-3,4-dihydroxybutyric acid, and treating the intermediate with HCl in a methanol solution. However, this process suffers from the disadvantage of being performed in a complicated batch type manner and brings about pollution of the environment. In addition, the use of sodium borohydride, an expensive and explosive reducing agent, increases the production cost and thus is not suitable for large-scale production. When being used in large quantities, ether employed as a reaction solvent may create a noxious effect on the body owing to its narcotic nature and has the danger of exploding.

In U.S. Pat. No. 5,998,633 is described a process for the preparation of substituted gamma-butyrolactone, in which a hydrocarbon is oxidized to give acetonide, followed by the treatment of the intermediate with an inorganic acid (aqueous HCl solution). This process is also industrially disadvantageous in that it is complicated and produces waste in large quantities.

As described above, the conventional processes are of batch types employing liquid or solid oxidizing or reducing reagents, so that they have the disadvantage of low productivity as well as the production of waste in large quantities. Furthermore, the conventional processes are limited in industrial applications since the low production yield is obtained owing to the complexity thereof.

SUMMARY OF THE INVENTION

Leading to the present invention, the intensive and thorough research on the production of optically active (S)-beta-hydroxy-gamma-butyrolactone, conducted by the present inventors, resulted in the finding that a catalyst, having as a catalytic ingredient a noble metal impregnated in an inorganic oxide support, for hydrogenating optically active, substituted carboxylic acid derivatives is very useful in synthesizing optically pure (S)-beta-hydroxy-gamma-butyrolactone and a fixed bed of the catalyst makes it possible to produce the compound of interest in a continuous manner.

Therefore, it is an object of the present invention to provide a process for the production of optically pure (S)-beta-hydroxy-gamma-butyrolactone from substituted carboxylic acid derivatives, which is improved in the production yield, friendly to the environment, and simple.

Based on the present invention, the above object could be accomplished by a provision of a method for producing optically pure (S)-beta-hydroxy-gamma-butyrolactone from a substituted carboxylic acid derivative by hydrogenation, in which a solution containing 1 to 50% by weight of the substituted carboxylic acid derivative is fed at a WHSV of 0.1 to 10 $h^{-1}$, to a fixed bed reactor which is filled with a catalyst and maintained at a reaction temperature of 50 to 550° C. under a hydrogen partial pressure of 15 to 5,500 psig, said catalyst having a noble metal as a catalytically effective ingredient and an inorganic oxide as a support, said hydrogen being maintained at a molar ratio of 1:1 to 10:1 relative to the substituted carboxylic acid derivative.

DETAILED DESCRIPTION OF THE INVENTION

Figure 1:
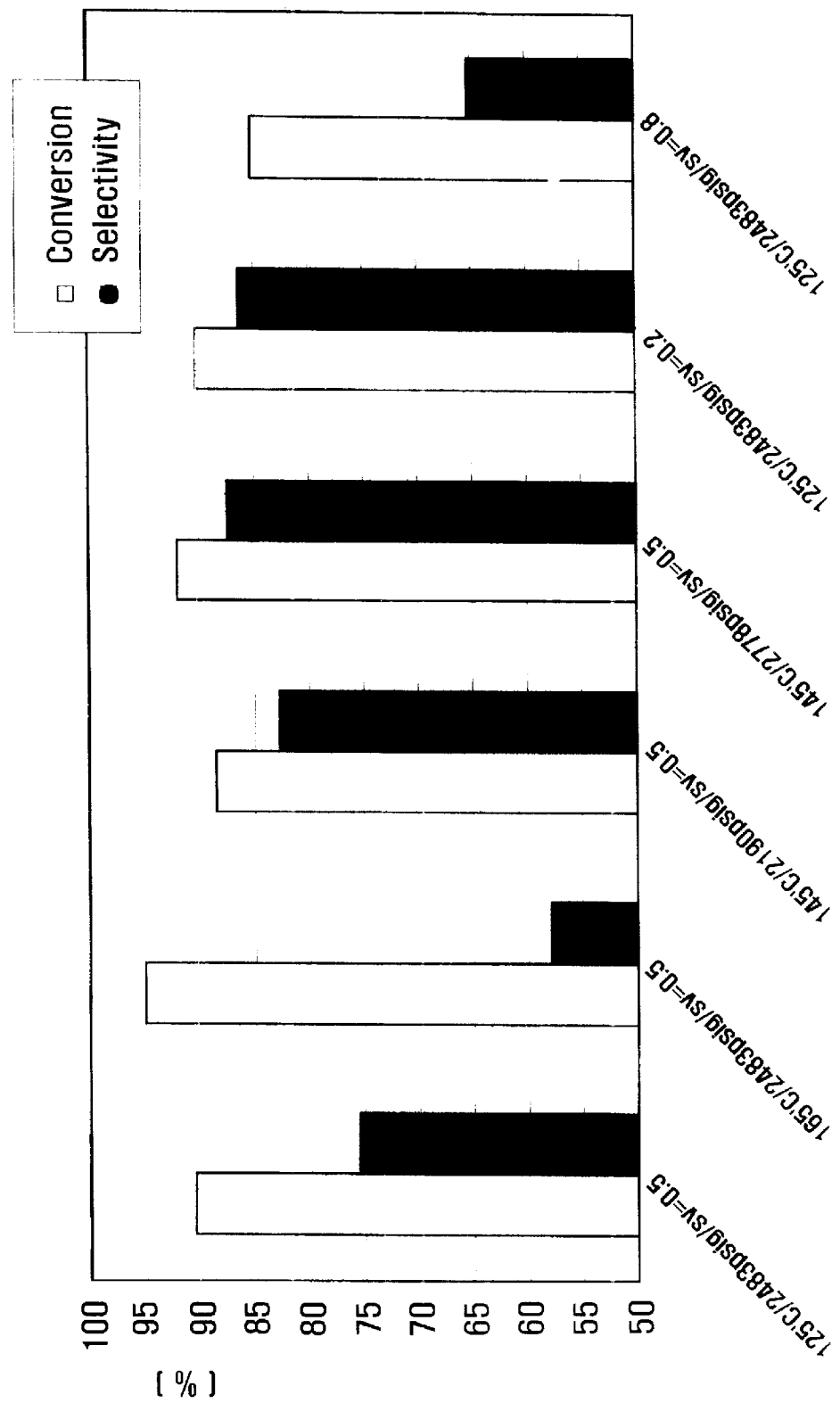
FIG. 1 is a histogram showing the conversion and selectivity under various reaction conditions when substituted carboxylic acid derivatives are converted to optically pure (S)-beta-hydroxy-gamma-butyrolactone by hydrogenation in the presence of a catalyst in accordance with the present invention.

The present invention pertains to continuous hydrogenation of esters of substituted carboxylic acids into optically pure (S)-beta-hydroxy-gamma-butyrolactone in the presence of a catalyst in a fixed bed reactor. By virtue of its superior production yield and productivity, this continuous process is far more economical than conventional processes. The process of the present invention also has an economical benefit in that the catalyst can be recovered and used repeatedly. Additionally, the above process requires no complicated post-processes, such as filtering off of the catalyst.

A catalyst suitable for use in the hydrogenation according to the present invention comprises a noble metal as a catalytically active ingredient. A useful noble metal is selected from the group consisting of nickel (Ni), palladium (Pd), platinum (Pt), rhodium (Rh), iridium (Ir), ruthenium (Ru), osmium (Os) and mixtures thereof. Such catalytically effective ingredient is impregnated on a support, which is preferably selected from the group consisting of alumina, silica, silica-alumina, zirconia, titania, zeolite and a molecular sieve.

The hydrogenation according to the present invention can be illustrated by the following reaction formula 1:

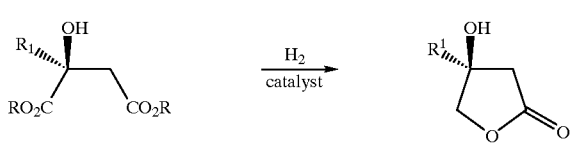

wherein R is a linear alkyl containing 1 to 10 carbon atoms, a cycloalkyl, or an aryl; and R' is a hydrogen atom or a methyl.

According to the present invention, to synthesize an ester compound of a substituted carboxylic acid from which optically pure (S)-beta-hydroxy-gamma-butyrolactone is produced, there is employed an alcohol selected from a linear alcohol containing 1 to 10 carbon atoms such as methanol, ethanol and n-propanol, a cycloalcohol or an aromatic alcohol. The alcohol is used at an amount of 2.0 to 40 equivalents of the carboxylic acid used. As for the carboxylic acid, for example, optically pure malic acid or citramalic acid may be used. The esterification reaction is carried out at 50 to 150° C. under a pressure of 1 to 300 psig with a weight hourly space velocity (WHSV) ranging from 0.1 to 10 $h^{-1}$ in the absence of or in the presence of a catalyst. Suitable as a catalyst is a solid acid with a preference to a sulfonate-substituted strong acid resin. If the reaction conditions are outside the above ranges, the production yield of the esters of carboxylic acid is lowered and the deactivation rate of the catalyst increases. Accordingly, the advantages that the continuous process of the present invention enjoys are lost.

In accordance with the present invention, the hydrogenation of esters of substituted carboxylic acid into optically active (S)-beta-hydroxy-gamma-butyrolactone is carried out at 50 to 550° C. under a hydrogen partial pressure of 15 to 5,500 psig with a WHSV ranging from 0.2 to 10 $h^{-1}$. This conversion through hydrogenation is preferably conducted at 100 to 250° C. under a hydrogen partial pressure of 1,000 to 4,000 psig with a WHSV ranging from 0.2 to 10 $h^{-1}$, and more preferably at 110 to 200° C. under a hydrogen partial pressure of 1,200 to 3,000 psig with a WHSV ranging from 0.3 to 5 $h^{-1}$. A reaction condition outside any of the ranges causes a decrease in the production yield and an increase in the deactivation rate of the catalyst, resulting in loss of the advantages that the continuous process of the present invention enjoys.

To completely convert an ester derivative of substituted carboxylic acid into a desired compound, the mole ratio of hydrogen to the ester derivative of substituted carboxylic acid is required to be at least 1.0. No limits are given to the amount of hydrogen if the mole ratio exceeds about 1. However, when an economical aspect is taken into consideration, the ratio of hydrogen to an ester of carboxylic acid is preferably maintained in the range from 2.0 to 10. The hydrogen which passes through the reactor while remaining unreacted is re-compressed and recycled into the reactor. Depending on reaction conditions, the reaction may be directly separated into desirable products or may be recycled to further convert the unreacted reactant, followed by separation.

To convert esters of substituted carboxylic acid into (S)-beta-hydroxy-gamma-butyrolactone by hydrogenation, there is required a solvent suitable for dissolving highly viscous carboxylic derivatives so effectively as to smoothly feed them to the reactor. Further, the solvent requires to remove the heat of reaction which occurs during the esterification and the hydrogenation and not to react with any of the reactants, e.g., neither carboxylic acid derivatives nor hydrogen. For example, one selected from the group consisting of methyl alcohol, ethyl alcohol, n-propyl alcohol, isopropyl alcohol, dioxane, gamma-butyrolactone, tetrahydrofuran, water and mixtures thereof may be used as a solvent. Of these, isopropyl alcohol and water are preferred with greater preference for the latter. In the solvent, the ester of carboxylic acid is maintained at a concentration of 1 to 50% by weight and preferably at a concentration of 10 to 40% by weight.

As mentioned above, the hydrogenation according to the present invention is conducted with the aid of a catalyst. This has a noble metal as a catalytically effective ingredient. Examples of suitable noble metals include Ni, Pd, Pt, Rh, Ir, Ru, Os and mixtures thereof with preference to Ru. The catalytically active ingredient may be used in a bare form or in a combination with a support. In the latter case, the noble metal is impregnated on the support. Suitable as a support is an inorganic oxide selected from the group consisting of alumina, silica, silica-alumina, zirconia, titania, zeolite and molecular sieves. Of them, silica is most preferred.

The support may be in any form, such as a spherical form, a cylindrical form, a granular form, etc. For mechanical properties, the support preferably has a spherical or a cylindrical form.

In the catalyst, the noble metal is preferably contained at an amount of 0.1 to 15% by weight based on the catalyst, and more preferably at an amount of 0.5 to 10% by weight. For instance, a catalyst containing less than 0.1% by weight of the noble metal is poor in hydrogenation activity and selectivity. On the other hand, more than 15% by weight of the noble metal is economically unfavorable.

For impregnating the noble metal into the support, there may be used various techniques, including incipient wetness impregnation, excess water impregnation, spraying, and physically mixing. After completion of the impregnation, the composite is sintered for 2 hours or more in the air or an inert gas atmosphere. The sintering temperature is preferably maintained at 300 to 700° C. and more preferably at 300 to 550° C. For instance, when the sintering is carried out at less than 300° C., precursors of the metal impregnated are insufficiently decomposed. On the other hand, a sintering temperature higher than 700° C. lowers the dispersion degree of the metal impregnated, resulting in a catalyst with poor performance.

In a fixed bed reactor is filled the sintered catalyst. Before feeding the reactant to the reactor, the catalyst should be in a reduced state. To this end, the catalyst is maintained for at least 2 hours in a hydrogen atmosphere at 50 to 500° C. depending on the kind of the metal impregnated.

In the presence of the catalyst system which has a noble metal impregnated in a support, substituted carboxylic acid derivatives are hydrogenated to give optically pure (S)-beta-hydroxy-gamma-butyrolactone at a high yield. In accordance with the present invention, the employment of a fixed bed reactor in this hydrogenation allows the process to be conducted in a continuous manner, bringing about a great improvement in the production yield. In addition, the process is economically favorable in that the used catalyst may be recovered easily. Furthermore, the product recovery following the conversion is simple because there is no need to filter off the catalyst.

By adopting a fixed bed reaction system, the present invention shows a higher production yield per reactive space time than do conventional processes, has an economical benefit owing to the repeated use of the catalyst, and is simple without the need of filtering off the catalyst upon recovering the product. In the fixed bed reaction system, no limitations are imposed as to the form of the reactor or the reactant feeding and flowing direction. In order for reactants to come in smooth contact with each other, a trickle-bed type reactor is preferably used in which the reactants hydrocarbon and hydrogen are flowed downward together and dispersed uniformly throughout.

Effluents from the reactor are passed to a solvent-recovering unit in which the solvent is at least partially separated from the product. For this purpose, any recovering unit, such as a distillation column or a flash vaporizer, may be provided to the reactor system. Products or concentrates drained from the lower portion of the recovering unit are transferred to a vacuum distillation unit.

A better understanding of the present invention may be obtained in light of the following examples which are set forth to illustrate, but are not to be construed to limit the present invention.

EXAMPLE 1

Preparation of Catalyst

In a 100 cc flask containing secondary distilled water was added 17.9 g of ruthenium chloride ($RuCl_3$) to give a aqueous ruthenium solution. In a vessel for impregnating metal, equipped with a speed-controllable motor, 100 g of silica (⅛ cylindrical) was added, after which the ruthenium solution was poured while rotating the vessel. As a result, the ruthenium solution was uniformly dispersed over the silica. For 30 min, after completion of the pouring of the ruthenium solution, the vessel was further rotated at the same speed. Subsequently, the resulting ruthenium-supported catalyst was sintered at 550° C. for 6 hours under the air atmosphere in a muffle furnace. The catalyst was found to have a ruthenium content of 3.0% by weight as measured by fluorescent X-ray analysis.

EXAMPLE 2

Continuous Preparation of Dimethyl (S)-Malate

In an automatic high-pressure reactor made of stainless steel 316 was filled 25 g of a solid acid catalyst. After being purged with nitrogen, the inside of the reactor was heated from room temperature to 84° C. and maintained at a pressure of 100 psig. L-malic acid was dissolved in 8 equivalents of methanol and the resulting solution was fed at a WHSV of 4.0 $h^{-1}$ into the reactor to produce the title compound at a yield of 90%: Conversion 99%. Selectivity 99%.

The effluent from the reactor was distilled in vacuum to separate at a separation yield of 90% dimethyl (S)-malate which was 99.8% in purity and 99.9% in optical purity. The preparation could be effected in a batch type. In this case, the reaction period of time was set to be 2 to 4 hours.

EXAMPLES 3 THROUGH 8

Continuous Preparation of (S)-Beta-Hydroxy-Gamma-Butyrolactone

In an automatic, stainless-steel 316, high pressure reactor (inner diameter 2.52 cm×length 60 cm) was filled 50 g of the catalyst prepared in Example 1. The catalyst was converted to a reduced state by raising the temperature at a rate of 1° C. per min to 350° C. and maintained at this temperature for 6 hours in a hydrogen atmosphere. After being cooled, the inside of the reactor was purged with nitrogen gas. While the inside of the reactor was heated at a rate of 1° C. per min to 145° C. from room temperature, hydrogen was fed at a rate of 100 sccm. The hydrogen was added at an amount twice as much as necessary for the reaction. The dimethyl (S)-malate prepared in Example 2 was dissolved in water to give a 30 wt % solution. This dimethyl (S)-malate solution was fed under the conditions shown in Table 1, below. Reaction products were taken every 9 hours and analyzed by gas chromatography using a flame ionization detector (FID) (beta-DEX column 60 cm×0.25 mm×0.25 μm). The results are given in Table 1, below.

TABLE 1

| Exam. No | Temp. (° C.) | Press. (psig) | WHSV ($h^{-1}$) | Conversion (%) | Selectivity for S)-HGB* (%) |
|---|---|---|---|---|---|
| 3 | 125 | 2,483 | 0.5 | 90.5 | 75.5 |
| 4 | 165 | 2,483 | 0.5 | 95.0 | 57.9 |
| 5 | 145 | 2,190 | 0.5 | 88.5 | 82.7 |
| 6 | 145 | 2,778 | 0.5 | 92.0 | 87.5 |
| 7 | 125 | 2,483 | 0.2 | 90.2 | 86.3 |
| 8 | 125 | 2,483 | 0.8 | 85.2 | 65.3 |

*(S)-beta-hydroxy-γ-butyrolactone

EXAMPLES 9 THROUGH 12

Continuous Preparation of (S)-beta-Hydroxy-gamma-Butyrolactone

While the solvent was being changed as shown in Table 2, below, the hydrogenation of dimethyl (S)-malate was conducted at 145° C. under a hydrogen partial pressure of 2,628 psig with the reactant being fed at a WHSV of 0.5 $h^{-1}$ in the same manner as in Example 3. A measurement was made of the conversion and selectivity and the results are given in Table 2, below.

TABLE 2

| Example No. | Solvent | Conversion. (%) | Selectivity for(S) - HGB* (%) |
|---|---|---|---|
| 9 | 30% $H_2O$ | 92.0 | 85.5 |
| 10 | 20% $H_2O$ | 94.0 | 72.0 |
| 11 | 10% $H_2O$ | 95.0 | 78.0 |
| 12 | 10% i-PrOH | 72.5 | 54.2 |

*(S)-beta-hydroxy-γ-butyrolactone

EXAMPLE 13

Low-Pressure Hydrogenation and Product Recycling

In the presence of the catalyst prepared in Example 1, the hydrogenation process was carried out in the same manner as in Example 6, except using a hydrogen partial pressure of as low as 1,460 psig. Product effluents from the reactor were recycled twice more. During the recycling, no deactivation of the catalyst was observed while an improvement was brought about in the conversion and selectivity. The results are given in Table 3, below.

TABLE 3

| Rxn Cycle No. | Conversion (%) | Selectivity (%) |
| --- | --- | --- |
| 1 | 75 | 65 |
| 2 | 90 | 75 |
| 3 | 95 | 85 |

EXAMPLE 14

Long-Term Continuous Reaction for (S)-beta-Hydroxy-gamma-Butyrolactone

Using the catalyst prepared in Example 1, a long-term continuous conversion reaction was performed in a reactor similar to that described in Example 2. Even after 500 hours of the reaction, no deactivation was observed in the catalyst. The results are given in Table 4, below.

TABLE 4

| | Rxn Time (h) | | |
| --- | --- | --- | --- |
| | 100 | 250 | 500 |
| Conversion (%) | 92.5 | 92.4 | 91.4 |
| Selectivity (%) | 74.3 | 78.8 | 77.7 |

EXAMPLE 15

Separation of (S)-beta-Hydroxy-gamma-Butyrolactone

Using 50 g of the catalysts prepared in Example 1, a hydrogen reaction was conducted in a reactor similar to that described in Example 2. During hydrogenation, the hydrogen partial pressure was maintained at 2,438 psig while there were various changes to the reaction temperature and the WHSV. After 200 hours of the hydrogenation, 30 liters of a solution containing (S)-beta-hydroxy-gamma-butyrolactone with a selectivity of 75.2 wt % was obtained. This solution was neutralized with an aqueous 10% $NaHCO_3$ solution and deprived of the solvent, after which the residue was extracted three times with ethyl acetate to recover (S)-beta-hydroxy-gamma-butyrolactone. In 10 L glass reactor equipped with a vacuum distillater, the extract was distilled at 60° C. under 100 mbar to evaporate the solvent. In a thin film evaporator, the concentrate was further distilled at 100 to 120° C. under 0.6 to 1.7 torr to give (S)-beta-hydroxy-gamma-butyrolactone 99.0% in purity at a separation yield of 65%.

As described hereinbefore, the present invention can produce optically pure (S)-beta-hydroxy-gamma-butyrolactone with higher purities at higher yields than can conventional techniques. In addition to being relatively simple and environmentally friendly, the present invention is so economically favorable as to apply to industrial production.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for producing optically pure (S)-beta-hydroxy-gamma-butyrolactone from a substituted carboxylic acid derivative by hydrogenation, in which a solution containing 1 to 50% by weight of the substituted carboxylic acid derivative is fed at a WHSV of 0.1 to 10 $h^{-1}$, to a fixed bed reactor which is filled with a catalyst and maintained at a reaction temperature of 50 to 550° C. under a hydrogen partial pressure of 15 to 5,500 psig, said catalyst having a noble metal as a catalytically effective ingredient and an inorganic oxide as a support, said hydrogen being maintained at a molar ratio of 1:1 to 10:1 relative to the substituted carboxylic acid derivative.

2. The method as set forth in claim 1, wherein said noble metal is selected from the group consisting of palladium (Pd), platinum (Pt), rhodium (Rh), iridium (Ir), ruthenium (Ru), osmium (Os), and mixtures thereof.

3. The method as set forth in claim 1, wherein the noble metal is impregnated on the inorganic acid support at an amount of 0.1 to 15% by weight based on the catalyst.

4. The method as set forth in claim 1, wherein said reaction temperature is maintained at 100 to 250° C.

5. The method as set forth in claim 1, wherein said hydrogen partial pressure is maintained at 1,200 to 3,000 psig.

6. The method as set forth in claim 1, wherein the reactants are fed at a WHSV of 0.2 to 5.0 $h^{-1}$.

7. The method as set forth in claim 1, wherein said solution contains the carboxylic acid derivative at an amount of 10 to 40% by weight.

8. The method as set forth in claim 1, wherein said solvent is selected from the group consisting of methyl alcohol, ethyl alcohol, n-propyl alcohol, isopropyl alcohol, dioxane, gamma butyrolactone, tetrahydrofuran, water and mixtures thereof.

9. The method as set forth in claim 1, wherein said inorganic oxide support is selected from the group consisting of alumina, silica, silica-alumina, zirconia, titania, zeolite and molecular sieves.

10. The method as set forth in claim 1, wherein said fixed bed reactor is a trickle-bed reactor.

11. The method as set forth in claim 1, wherein said substituted carboxylic acid derivative is prepared by reacting a carboxylic acid with an alcohol in the presence of a solid acid in a reactor which is maintained at a reaction temperature of 50 to 150° C. under a reaction pressure of 1.0 to 300 psig with a WHSV being controlled within the range of 0.5 to 10 $h^{-1}$, said alcohol being selected from the group consisting of linear alcohols containing 1 to 10 carbon atoms, cyclic alcohols and aromatic alcohols and being used at an amount of 2.0 to 40 equivalents of said carboxylic acid.

12. The method as set forth in claim 11, wherein said solid acid is a sulfonate-substituted strong acidic resin.

13. The method as set forth in claim 11, wherein said carboxylic acid is optically pure malic acid or citramalic acid.

* * * * *